United States Patent [19]

Monticello et al.

[11] Patent Number: 5,358,870
[45] Date of Patent: Oct. 25, 1994

[54] MICROEMULSION PROCESS FOR DIRECT BIOCATALYTIC DESULFURIZATION OF ORGANOSULFUR MOLECULES

[75] Inventors: Daniel J. Monticello, The Woodlands, Tex.; John J. Kilbane, II, Woodstock, Ill.

[73] Assignees: Institute of Gas Technology, Chicago, Ill.; Energy BioSystems Corporation, The Woodlands, Tex.

[21] Appl. No.: 897,314

[22] Filed: Jun. 11, 1992

Related U.S. Application Data

[63] Continuation-in-part of Ser. No. 486,597, Feb. 28, 1990, Pat. No. 5,132,219.

[51] Int. Cl.$^5$ ............ C10G 32/00; C12N 9/14; C12N 1/12; C12N 1/00
[52] U.S. Cl. .................... 435/282; 435/195; 435/252.1; 435/252.7; 435/243; 435/832; 435/822
[58] Field of Search ............ 435/282, 195, 252.1, 435/252.31, 243, 832, 822

[56] References Cited

U.S. PATENT DOCUMENTS

| | | | |
|---|---|---|---|
| 2,975,103 | 3/1961 | Kirshenbaum | 435/282 |
| 4,283,270 | 8/1981 | McHale | 208/50 |
| 4,562,156 | 12/1985 | Isbister et al. | 435/253 |
| 4,618,348 | 10/1986 | Hayes | 44/51 |
| 4,632,906 | 12/1986 | Kopacz | 435/282 |
| 4,659,670 | 4/1987 | Stevens et al. | 435/262 |
| 4,808,535 | 2/1989 | Isbister | 435/252.1 |
| 4,851,350 | 7/1989 | Stevens, Jr. et al. | 435/262 |
| 5,002,888 | 3/1991 | Kilbane, II | 435/252.3 |
| 5,092,909 | 3/1992 | Werner et al. | 44/622 |
| 5,094,668 | 3/1992 | Kern et al. | 44/622 |
| 5,104,801 | 4/1992 | Kilbane, II | 435/282 |
| 5,132,219 | 7/1992 | Kilbane, II | 435/195 |
| 5,196,129 | 3/1993 | Luisi | 252/49.5 |
| 5,198,341 | 3/1993 | Kilbane, II | 435/42 |
| 5,232,854 | 8/1993 | Monticello | 435/282 |

FOREIGN PATENT DOCUMENTS

| | | |
|---|---|---|
| 0396832 | 11/1990 | European Pat. Off. |
| 0401922 | 12/1990 | European Pat. Off. |
| 0409314 | 1/1991 | European Pat. Off. |
| 0441462 | 8/1991 | European Pat. Off. |
| 0445896 | 9/1991 | European Pat. Off. |
| 92/16602 | 10/1992 | PCT Int'l Appl. |
| 92/19700 | 11/1992 | PCT Int'l Appl. |

OTHER PUBLICATIONS

Sagardia et al. (Jun. 1975) 29 Appl. Microbiol. (No. 6) 722–725.
Bertrand et al. (1983), 5 Biotechnol. Lett. (No. 8) 567–572.
Jack (1984), 100 Chem. Abstr. 153 (No. 100:54191q).
Hartdegen et al. (May 1984) 80 Chem. Eng. Prog. (No. 5) 63–67.

(List continued on next page.)

Primary Examiner—David M. Naff
Assistant Examiner—Mike Meller
Attorney, Agent, or Firm—Hamilton, Brook, Smith & Reynolds

[57] ABSTRACT

A method of desulfurizing a petroleum liquid containing organosulfur molecules is disclosed. The method relies upon the use of an aqueous biocatalytic agent comprising, in preferred embodiments, a substantially cell free extract of a microorganism which functionally expresses an enzyme capable of selectively cleaving organic carbon-sulfur bonds even in sulfur-bearing heterocycles, wherein the extract contains a substantial proportion of the total activity of said enzyme expressed by the microorganism. An emulsion, preferably a microemulsion, is formed between this biocatalytic agent and the petroleum liquid. Reversible microemulsions are particularly preferred, due to facilitated recovery of a desulfurized petroleum liquid at the conclusion of treatment. The invention described is particularly well suited to the desulfurization of petroleum liquids having a high relative abundance of refractory organosulfur molecules, such as dibenzothiophene.

20 Claims, 2 Drawing Sheets

OTHER PUBLICATIONS

Kargi and Robinson (Jul. 1984) 26 Biotechnol. Bioeng. 687-690.
Monticello and Finnerty (1985) 39 Ann. Rev. Microbiol. 371-389.
Isbister and Kobylinski (1985) 9 Coal Sci. Technol. 627-641.
Monticello et al. (Apr. 1985) 49 Appl. Env. Microbiol. (No. 4) 756-760.
Kargi (1987) 107 Chem. Abstr. 147 (No. 107:118128d).
Bhadra et al. (1987) 5 Biotech. Adv. 1-27.
Kitchell et al. (1989) Processing and Bioprocessing of Fossil Fuels Workshop 297-307 (Bayer, ed).
Kilbane II (Apr. 1989) 7 Trends Biotechnol. (vol. 4) 97-101.
Lee and Yen (1990) 48 J. Chem. Tech. Biotechnol. 71-79.
Kilbane II (1990) 3 Resour. Conserv. Recycl. 69-79.
Ochman et al. (1990) 63 Microbios 79-91.
Larsson et al. (Jun. 1990) 36 Biotechnol. Bioeng. 135-141.
Stoner et al. (Sep. 1990) 56 Appl. Env. Microbiol. (No. 9) 2667-2676.
Kilbane II (Sep. 10-14, 1990) 7th Int'l. Pittsburgh Coal Conf., Pittsburgh, PA 373-383.
Shih et al. (Nov. 12, 1990) Chicago Ann. Mtg., Amer, Inst. Chem. Eng. Abstract No. 264B (monograph; full text available upon request to the Amer. Inst. Chem. Eng.).
Monticello and Kilbane II (Dec. 3-5, 1990) 3rd Int'l. Symp. on Gas, Oil, Coal and Env. Biotechnol., New Orleans, LA 1-12.
Khalid et al. (1991) 5 Resour. Conserv. Recycl. 167-181.
Dordick et al. (1991) 5 Resour. Conserv. Recycl. 195-209.
Omori et al. (Mar. 1992) 58 Appl. Env. Microbiol. (No. 3) 911-915.
van Afferden et al. (1990), Arch. Microbiol. 153:324-328.
Crawford and Gupta (1990) Current Microbiol. 21:229-231.
MacMichael et al.; *Applied Environmental Microbiology,* vol. 53, No. 1, Jan. 1987, pp. 65-69.

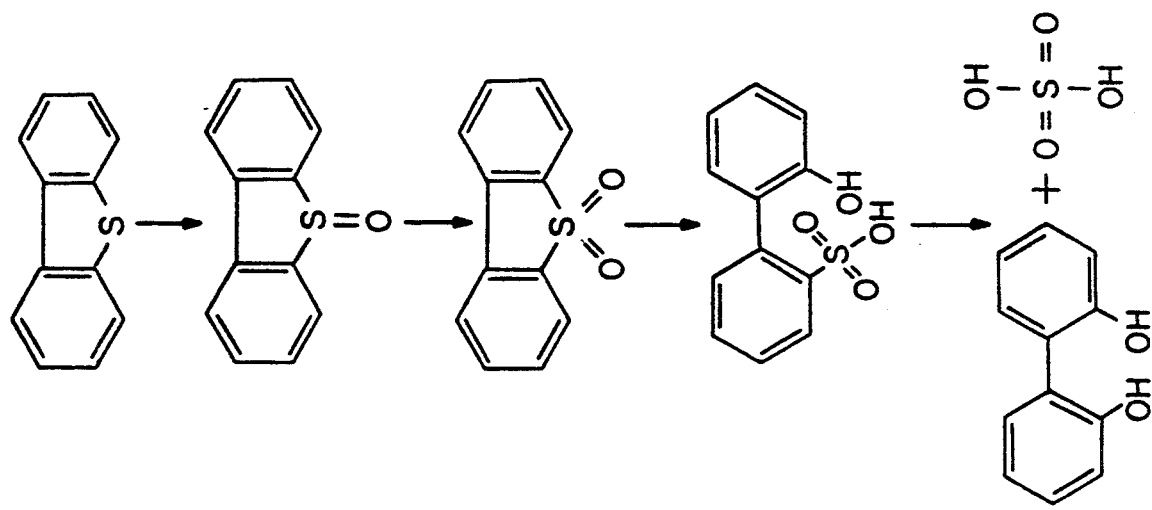
Fig. 3
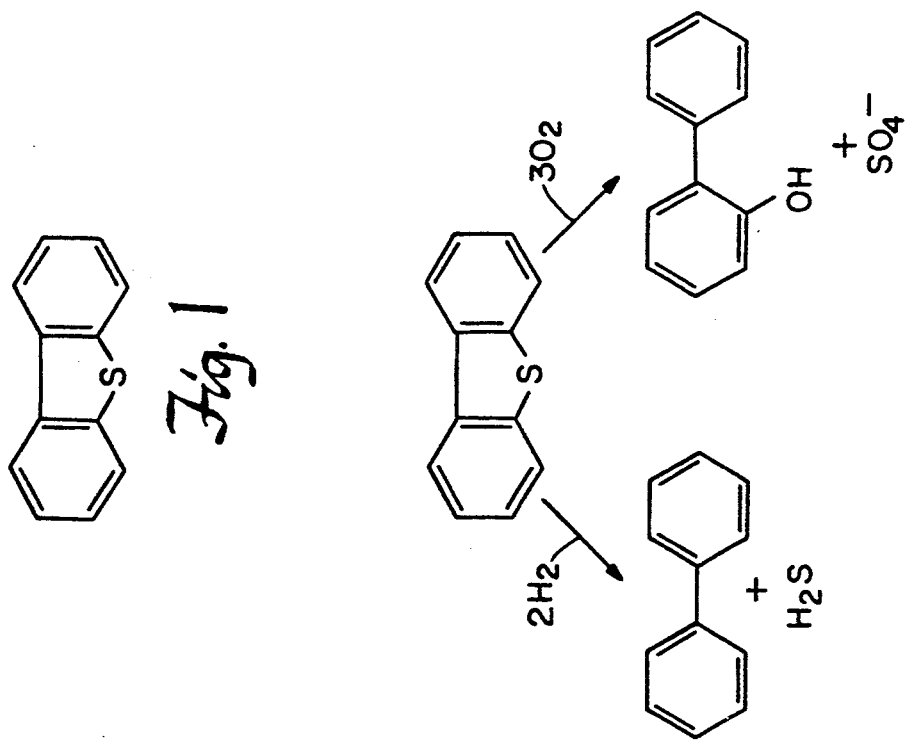
Fig. 1
Fig. 2

MICROEMULSION PROCESS FOR DIRECT BIOCATALYTIC DESULFURIZATION OF ORGANOSULFUR MOLECULES

RELATED APPLICATION

This is a continuation-in-part of U.S. Pat. application Ser. No. 07/486,597, filed on Feb. 28, 1990, entitled "BACTERIAL PRODUCED EXTRACTS AND ENZYMES FOR CLEAVAGE OF ORGANIC C—S BONDS", which has now issued as U.S. Pat. No. 5,132,219 on Jul. 21, 1992 teachings of which are incorporated herein by reference.

BACKGROUND

Sulfur is an objectionable element which is nearly ubiquitous in fossil fuels, where it occurs both as inorganic (e.g., pyritic) sulfur and as organic sulfur (e.g., a sulfur atom or moiety present in a wide variety of hydrocarbon molecules, including for example, mercaptans, disulfides, sulfones, thiols, thioethers, thiophenes, and other more complex forms). Organic sulfur can account for close to 100% of the total sulfur content of petroleum liquids, such as crude oil and many petroleum distillate fractions. Crude oils can typically range from close to about 5 wt % down to about 0.1 wt % organic sulfur. Those obtained from the Persian Gulf area and from Venezuela (Cerro Negro) can be particularly high in organic sulfur content. Monticello, D. J. and J. J. Kilbane, "Practical Considerations in Biodesulfurization of Petroleum", *IGT's 3rd Intl Symp. on Gas, Oil, Coal, and Env. Biotech.*, (Dec.3-5, 1990) New Orleans, La., and Monticello, D. J. and W. R. Finnerty, (1985) *Ann. Rev. Microbiol.* 39:371-389.

The presence of sulfur in fossil fuels has been correlated with the corrosion of pipeline, pumping, and refining equipment, and with premature breakdown of combustion engines. Sulfur also contaminates or poisons many catalysts which are used in the refining and combustion of fossil fuels. Moreover, the atmospheric emission of sulfur combustion products such as sulfur dioxide leads to the form of acid deposition known as acid rain. Acid rain has lasting deleterious effects on aquatic and forest ecosystems, as well as on agricultural areas located downwind of combustion facilities. Monticello, D. J. and W. R. Finnerty, (1985) *Ann. Rev. Microbiol.* 39:371-389. To combat these problems, several methods for desulfurizing fossil fuels, either prior to or immediately after combustion, have been developed.

One technique which is employed for pre-combustion sulfur removal is hydrodesulfurization (HDS). This technique is suitable for the desulfurization of fluid fossil fuels wherein sulfur is present in predominantly organic, rather than pyritic, form. HDS is thus useful for treating petroleum distillate fractions or refining intermediates, liquid motor fuels, and the like. The HDS process involves reacting the sulfur-containing fossil fuel with hydrogen gas in the presence of a catalyst, usually cobalt- or molybdenum-aluminum oxide or a combination thereof, at elevated temperature and pressure. HDS is more particularly described in Shih, S.S. et al., "Deep Desulfurization of Distillate Components", Abstract No. 264B AIChE Chicago Annual Meeting, presented Nov.12, 1990, (complete text available upon request from the American Institute of Chemical Engineers; hereinafter Shih et al.), Gary, J. H. and G. E. Handwerk, (1975) *Petroleum Refining: Technology and Economics*, Marcel Dekker, Inc., New York, pp. 114-120, and Speight, J. G., (1981) *The Desulfurization of Heavy Oils and Residue*, Marcel Dekker, Inc., New York, pp. 119-127. HDS is based on the reductive conversion of organic sulfur into hydrogen sulfide ($H_2S$), a corrosive gaseous product which is removed from the fossil fuel by stripping. Elevated or persistent levels of hydrogen sulfide are known to inactivate or poison the chemical HDS catalyst, complicating the desulfurization of high-sulfur fossil fuels.

It is also known that the efficacy of HDS treatment for particular types of fossil fuels and refining fractions varies due to the wide chemical diversity of hydrocarbon molecules which can contain sulfur atoms or moieties. Some classes of organic sulfur molecules are labile and can be readily desulfurized by HDS; other classes are refractory and resist desulfurization by HDS treatment. The classes of organic molecules which are often labile to HDS treatment include mercaptans, thioethers, and disulfides. Conversely, the aromatic sulfur-bearing heterocycles (i.e., aromatic molecules bearing one or more sulfur atoms in the aromatic ring structure itself) are the major class of HDS-refractory organic sulfur-containing molecules. Typically, the HDS-mediated desulfurization of these refractory molecules proceeds only at temperatures and pressures so extreme that valuable hydrocarbons in the fossil fuel or refining fraction can begin to deteriorate. Shih et al.

Recognizing these and other shortcomings of HDS, many investigators have pursued the development of commercially viable techniques of microbial desulfurization (MDS). MDS is generally described as the harnessing of metabolic processes of suitable bacteria to the desulfurization of fossil fuels. Thus, MDS typically involves mild (e.g., ambient or physiological) conditions, and does not involve the extremes of temperature and pressure required for HDS. It is also generally considered advantageous that biological desulfurizing agents can renew or replenish themselves under suitable conditions.

The discovery that certain species of chemolithotrophic bacteria, most notably *Thiobacillus ferrooxidans*, can obtain energy for metabolic processes from the oxidation of pyritic (inorganic) sulfur into water-soluble sulfate has spurred efforts to develop an MDS technique suitable for desulfurizing coal, a fossil fuel in which pyritic sulfur is known to generally predominate. For example, Detz, C. M. and G. Barvinchak U.S. Pat. No. 4,206,288 (issued 1980) describe an aerobic fermentation method for the microbial desulfurization of a coal slurry based upon the metabolic properties of actively growing *T. ferrooxidans* organisms. Recently, Madgavkar, A. M. U.S. Pat. No. 4,861,723 (issued 1989), has proposed a continuous *T. ferrooxidans*-based MDS method for desulfurizing particulate coal and preparing a clean burning desulfurized coal-water admixture. Despite this progress, a commercially viable MDS process for desulfurizing coal has not yet emerged, due in part to the time (days to weeks) required for the desulfurizing fermentation step.

As noted previously, *T. ferrooxidans*-mediated MDS techniques are restricted to the treatment of fossil fuels in which inorganic sulfur, rather than organic sulfur, predominates. Progress in the development of an MDS technique appropriate for the desulfurization of fossil fuels in which organic sulfur predominates has not been as promising. Several species of bacteria have been reported to be capable of catabolizing (metabolically breaking down) sulfur-containing hydrocarbons into water-soluble sulfur products. One early report in this field describes a cyclic catabolic MDS process employing cultures of *Thiobacillus thiooxidans, Thiophyso volutans,* or *Thiobacillus thioparus* as the microbial agent. Kirshenbaum, I., U.S. Pat. No. 2,975,103 (issued 1961). Subsequently, Monticello, D. J. and W. R. Finnerty, (1985) *Ann. Rev. Microbiol.* 39:371–389, and Hartdegan, F. J. et al., (May 1984) *Chem. Eng. Progress* 63–67, reported that such MDS processes are, for the most part, merely incident to the metabolic consumption of the hydrocarbon matrix by the microorganisms, rather than sulfur-selective or sulfur-specific phenomena. Moreover, catabolic MDS proceeds most readily on the classes of organic sulfur molecules described above as labile to HDS.

Although Monticello and Finnerty report that several species of bacteria, in particular *Pseudomonas putida* and *P. alcaligenes,* have been described as capable of desulfurizing HDS-refractory aromatic sulfur-bearing heterocycles, this reactivity is also merely incident to the consumption of these molecules as a carbon source. Consequently, in catabolic MDS, valuable combustible hydrocarbons are lost. Monticello and Finnerty additionally point out that the water-soluble sulfur products generated from the catabolic MDS of sulfur-bearing heterocycles are small organic molecules rather than inorganic sulfur ions. In view of these findings, the authors conclude that the commercial viability of MDS technology is limited. Monticello, D. J. and W. R. Finnerty, (1985) *Ann. Rev. Microbiol.* 39:371–389.

None of the above-described desulfurization technologies provides a commercially viable means for liberating sulfur from refractory organic molecules, such as the sulfur-bearing heterocycles, without a concomitant unacceptable deterioration of the fuel value of the treated (desulfurized) product. The interests of those actively engaged in the refining and manufacturing of petroleum fuel products have accordingly become focused on the need to identify such a desulfurization method. This need is driven in part by the prevalence of HDS refractory molecules in crude oils derived from such diverse locations as the Middle East (wherein about 40% of the total organic sulfur content is present in aromatic sulfur-bearing heterocycles) and West Texas (where such molecules account for up to about 70% of the total sulfur), and in part by the increasing stringency of environmental regulations pertaining to the combustion of sulfur-containing fossil fuels.

SUMMARY OF THE INVENTION

This invention relates to a method of desulfurizing a petroleum liquid which contains organic sulfur molecules. The present method relies on the use of an aqueous catalytic agent which is capable of selectively cleaving organic carbon-sulfur bonds even in sulfur-bearing heterocycles. In the invention described herein, an emulsion is formed between this catalytic agent and the petroleum liquid to be desulfurized. The emulsion is subsequently incubated under conditions sufficient to bring about the catalytic cleavage of organic carbon-sulfur bonds even in sulfur-bearing heterocycles, for a sufficient period of time for a significant number of catalytic cleavages to occur, whereby the organic sulfur content of the petroleum liquid is significantly reduced. Thus, the method of the present invention produces a desulfurized petroleum liquid, by which is meant a petroleum liquid substantially reduced in organic sulfur content, and particularly, one substantially depleted of sulfur-bearing heterocycles.

In preferred embodiments, the present invention relies upon the use of an aqueous biocatalytic agent, which is capable of carrying out the selective oxidative cleavage of carbon-sulfur bonds, even in sulfur bearing heterocycles, under mild conditions of temperature and pressure. In the invention described herein, it is particularly preferred that the aqueous biocatalytic agent comprises a substantially cell-free extract of a microorganism which functionally expresses an enzyme capable of selectively cleaving organic carbon-sulfur bonds in sulfur-bearing heterocycles, wherein the extract contains a substantial proportion of the total activity of said enzyme expressed by the microorganism. Particularly suitable sources of this enzyme include, for example, a culture of *Rhodococcus rhodocchrous* bacteria, ATCC No. 53968, or a derivative (e.g. mutant) thereof, wherein the functionally expressed enzyme is a cell envelope-associated enzyme which directs the sulfur-selective, oxidative cleavage of organic carbon-sulfur bonds in sulfur-bearing heterocycles. Extracts comprising cell envelope and envelope fragments thus contain a substantial proportion of the total enzyme activity expressed by such microorganisms. As used herein, the term "cell envelope" is intended to comprise the bacterial cell wall and/or cell membrane.

Furthermore, preferred embodiments of the present invention include the formation of a microemulsion, by which is meant the formation of an emulsion wherein the average diameter of droplets of the dispersed or discontinuous phase are less than about 1 $\mu$m. It is preferable to use a minimal volume of the aqueous biocatalyst, such that a microemulsion is formed wherein the organic phase (the petroleum liquid) is the continuous phase and the aqueous biocatalyst is the dispersed or discontinuous phase. It is particularly preferable that the microemulsion be reversible, as, following the incubation period, the separation of the aqueous and organic phases is thereby facilitated. In another embodiment, the aqueous (biocatalyst) and organic phases are combined under conditions sufficient to form reverse micelles therebetween. Following the incubation period, the reverse micelles are exposed to conditions sufficient to disrupt them, whereby readily separable aqueous and organic phases are obtained. Thus, the invention described herein contemplates the expeditious recovery of a desulfurized petroleum liquid.

A particular advantage of the present invention is that it provides for the biocatalytic, rather than simply the microbial catabolic, desulfurization of petroleum liquids. As a result, the present invention significantly broadens the variety of petroleum liquids which can be converted into clean-burning fuel products. This is due in a first aspect to the fact that the present method for desulfurization alleviates the need to expose crude oils or petroleum distillate fractions containing a high relative abundance of organic sulfur-bearing molecules to HDS conditions harsh enough to degrade valuable, combustible hydrocarbons. In a second aspect, this advantage is also attributable to the fact that desulfurization according to the present invention proceeds without exposure of the petroleum liquid being treated to living microorganisms capable of breaking down the hydrocarbon matrix of the fuel as an undesired consequence of conventional MDS.

Another advantage of the present invention is that it can be readily integrated, at numerous stages and/or locations, into existing petroleum extraction, transport, storage, refining or processing facilities. The site and stage of the manufacturing process at which the present invention is employed will be determined in large part upon consideration of the particular type and volume of petroleum liquid for which biocatalytic desulfurization (BDS) treatment is desired.

BRIEF DESCRIPTION OF THE DRAWINGS

FIG. 1 is a schematic illustration of the structural formula of dibenzothiophene, a model HDS-refractory sulfur-bearing heterocycle.

FIG. 2 is a schematic illustration of the cleavage of dibenzothiophene by oxidative and reductive pathways, and the end products thereof.

FIG. 3 is a schematic illustration of the stepwise, sulfur-selective oxidation of dibenzothiophene along the proposed "4S" pathway of microbial metabolism.

DETAILED DESCRIPTION OF THE INVENTION

Figure 4:
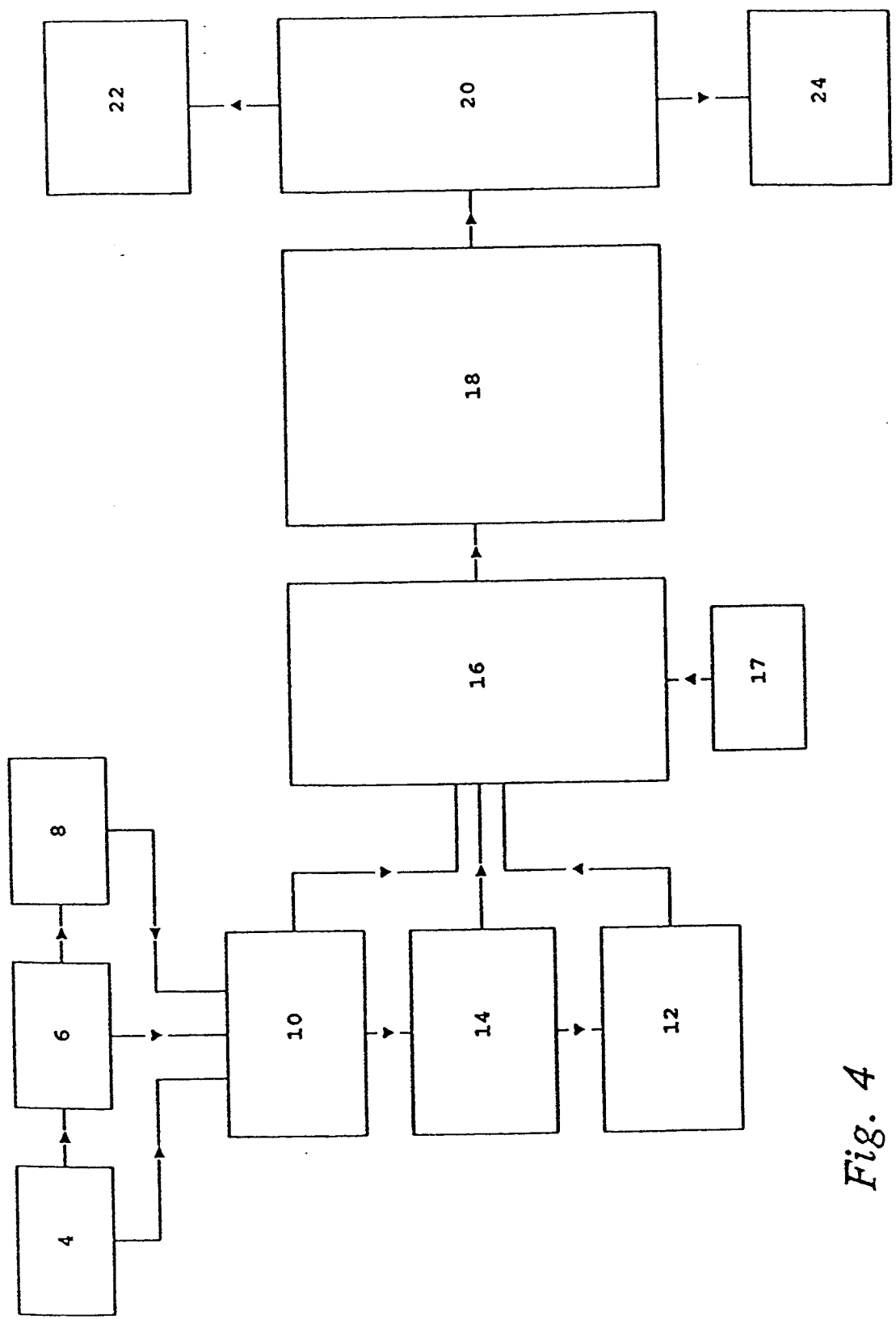
FIG. 4 is a process flow diagram illustrating the biocatalytic desulfurization method of the present invention.

The method presently described is one for the desulfurization of petroleum liquids wherein organic forms of sulfur comprise a significant proportion of the total sulfur content of the liquid. Thus, the present invention is suitable for the desulfurization of petroleum distillate fractions or refining intermediates, liquid motor fuels, and the like.

The method disclosed herein is unique in two aspects: first, it provides for the removal of organic sulfur from petroleum liquids without reliance on harsh chemical or physicochemical conditions, such as those required for desulfurization according to conventional HDS treatment; and second, it provides for the catalytic removal of organic sulfur from petroleum liquids without subjecting the substrate liquid to a lengthy and potentially deleterious fermentation step, such as that encountered in typical MDS processes. Because the present invention relies on catalysis, (in preferred embodiments, on biocatalysis) and not on general microbial metabolic activity, it is referred to herein as a biocatalytic desulfurization (BDS) method.

Without wishing to be limited as to the underlying mechanism for the instant BDS process, it is presumed that biocatalysis is carried out by at least one proteinaceous catalyst, commonly referred to as an enzyme, which acts upon sulfur-containing organic substrate molecules with a degree of selectivity characteristic of biological systems. The term "enzyme" as used herein is intended to encompass the biological composition of elements sufficient to produce BDS activity. Thus, "enzyme" includes one or more proteinaceous catalysts together with such coenzymes, cofactors, or coreactants as may be required to bring about the selective liberation of sulfur from organic molecules through the cleavage of organic carbon-sulfur bonds. A key aspect of the present invention is that it relies on the use of a biocatalyst which is capable of selectively cleaving carbon-sulfur bonds even in aromatic molecules. In preferred embodiments, biocatalytic cleavage proceeds through an oxidative pathway.

It is in the nature of biological systems to exhibit a degree of selectivity or specificity for certain types of sulfur-containing organic molecules. As noted above, a wide chemical diversity of such molecules are commonly encountered in petroleum liquids, including general classes of molecules having non-aromatic carbon-sulfur (e.g., thioether) bonds, aromatic carbon-sulfur bonds, or both. For present purposes, molecules having aromatic carbon-sulfur bonds are referred to as "sulfur-bearing heterocycles". These molecules are characterized by the presence of one or more sulfur atoms in the aromatic ring structure itself, rather than as a substituent thereof. The present biocatalyst is particularly useful in that unlike conventional microbial desulfurization agents, it is capable of selectively cleaving even aromatic carbon-sulfur bonds. Thus, it is particularly suitable for the desulfurization of a petroleum liquid in which sulfur-bearing heterocycles comprise a substantial proportion of the total organic sulfur content. Such a petroleum liquid is herein referred to as a "substrate" petroleum liquid, and is used to illustrate the advantages and utility of the present invention.

Sulfur-bearing heterocycles are generally refractory to both HDS and MDS treatment, and can occur in simple one-ring forms (e.g., thiophene, a five-membered compound having the composition $C_4H_4S$), or more complex multiple condensed-ring forms (e.g., the bicyclic compound benzothiophene, $C_8H_6S$). The difficulty of desulfurization of these molecules according to conventional techniques generally increases with increasing structural complexity. The tripartite condensed-ring sulfur-bearing heterocycle dibenzothiophene (DBT; $C_{12}H_8S$), shown in FIG. 1, is known to be particularly refractory to conventional HDS treatment, and therefore can constitute a major fraction of the residual post-HDS organic sulfur in fuel products. Alkyl-substituted DBT derivatives are even more refractory to conventional desulfurization processes, and cannot be removed even by repeated HDS processing under increasingly severe conditions. Shih et al. In addition, DBT and derivatives thereof can account for a significant percentage of the total organic sulfur in certain crude oils (e.g., of Kuwaiti and West Texas origin). For these reasons, DBT is generally viewed as a model refractory sulfur-bearing molecule in the development of new desulfurization methods. Monticello, D. J. and W. R. Finnerty, (1985) *Ann. Rev. Microbiol.* 39:371–389. Accordingly, the desulfurization of DBT is particularly relevant to the subject matter of the present invention; DBT serves herein as a preferred model for the biocatalytic desulfurization of substrate petroleum liquids.

Very few naturally occurring bacteria or other microbial organisms capable of effectively degrading or desulfurizing DBT have ever been reported. Recently, Stevens, S. E. and W. D. Burgess, U.S. Pat. No. 4,851,350 (issued 1989), reported the isolation from organic sulfur-enriched soil of strains of the yeasts *Hansenula sydowiorum, H. ciferrii, H. lynferdii*, and of the fungus *Cryptococcus albidus* said to be capable of removing "more than 60% of the sulfur in DBT in 48 hours." However, Stevens and Burgess do not discuss the possible mechanisms for this observed activity, and do not disclose whether the sulfur-containing products generated from DBT in the presence of *H. sydowiorum* are similar to those observed in conventional, catabolic MDS processes. It should be noted that organisms capable of totally degrading DBT appear to be quite rare in nature. For example, Gundlach, E. R. et al., (1983) *Science* 221:122–129 teaches that, when released into the environment, DBT and related complex heterocycles tend to persist for long periods of time and are not significantly biodegraded. Furthermore, the present inventors are unaware of any prior reports of the desulfurization of sulfur-bearing heterocycles by means a substantially cell-free lysate or extract of bacteria or other microbial organisms.

Several investigators have reported the genetic modification of naturally-occurring bacteria into mutant strains with the acquired capability of catabolizing DBT. Hartdegan, F. J. et al., (May 1984) *Chem. Eng. Progress* 63–67. For the most part, these mutants desulfurize DBT nonspecifically (by cleaving carbon-carbon bonds), and release sulfur in the form of small organic breakdown products. Thus, a portion of the fuel value (i.e., the hydrocarbon matrix) of DBT is lost through this microbial action (this is the metabolic activity underlying conventional MDS techniques). Isbister and Doyle reported the derivation of a mutant strain of Pseudomonas which appeared to be capable of selectively liberating sulfur from DBT. U.S. Patent No. 4,562,156 (issued 1985). However, they did not elucidate the mechanism responsible for this observed reactivity. As shown in FIG. 2, there are at least two possible pathways (oxidative and reductive) which result in the selective release of sulfur from DBT through the cleavage of carbon-sulfur bonds.

Kilbane recently reported the mutagenesis of a mixed bacterial culture, producing a bacterial consortium which appeared capable of selectively liberating sulfur from DBT by the oxidative pathway. *Resour. Cons. Recycl.* 3:69–79 (1990). This culture was composed of bacteria obtained from natural sources such as sewage sludge, petroleum refinery waste water, garden soil, coal tar-contaminated soil, etc., and maintained under conditions of continuous sulfur deprivation in the presence of DBT. The culture was then exposed to the chemical mutagen 1-methyl-3-nitro-1-nitrosoguanidine. The major catabolic product of DBT metabolism by the resulting microbial consortium was 2-hydroxybiphenyl: inorganic sulfur was released, while the hydrocarbon portion of the original molecule remained essentially intact.

A strain of *Rhodococcus rhodochrous* was isolated from the consortium. This strain, ATCC No. 53968, is a particularly preferred source of biocatalytic activity for use in the present method, in that it functionally expresses an enzyme capable of directing the selective, oxidative liberation of sulfur even from DBT and related sulfur-bearing heterocycles known to be present in petroleum liquids. Kilbane has described the isolation and characteristics of this strain in detail in U.S. Pat. No. 5,104,801 (issued 1992), the teachings of which are incorporated herein by reference. Strain ATCC No. 53968 was deposited under the Budapest Treaty on the International Recognition of the Deposit of Microorganisms for the Purposes of Patent Procedure on Nov. 28, 1989 with American Type Culture Collection, 12301 Parklawn Drive, Rockville, Md. 20852, U.S.A. In U.S. Pat. No. 5,002,888 (issued 1991), Kilbane describes the isolation and characteristics of another organic sulfur-selective microorganism, *Bacillus sphaericus* ATCC No. 53969, from the mixed culture described in *Resour. Cons. Recycl.* 3:69–79.

The "4S" reaction pathway has been proposed as a mechanism by which these products were generated; this pathway is summarized in FIG. 3. The designation "4S" refers to the reactive sulfur intermediates of the proposed pathway: DBT-sulfoxide, DBT-sulfone, DBT-sulfonate, and the liberated, water-soluble product, inorganic sulfate. Thus, in this biocatalytic pathway, the hydrocarbon portion of the molecule remains intact but for the cleavage of the two carbon-sulfur bonds by which the sulfur heteroatom is held in the central five-membered ring of DBT. In FIG. 3, the theoretical hydrocarbon product of this reaction pathway, dihydroxybiphenyl, is shown. In practice, however, 2-hydroxybiphenyl is observed using the ATCC No. 53968 culture. See Kilbane, J. J., (1990) *Resour. Cons. Recycl.* 3:69–79.

Generally speaking, the biocatalyst relied upon in this invention is obtained from an aqueous culture of a microorganism which functionally expresses an enzyme capable of selectively cleaving organic carbon-sulfur bonds even in sulfur-bearing heterocycles. A particularly preferable source of this biocatalyst comprises a culture of *R. rhodochrous* ATCC No. 53968 prepared under conditions sufficient to produce or maintain functional expression of biocatalytic activity, generally as described in U.S. Pat. No. 5,104,801. The embodiment of the invention which relies upon this particularly preferred biocatalyst is schematically depicted in FIG. 4, and will now be described. However, it should be noted that the scope and spirit of the present invention encompass, in preferred embodiments, the use of any microorganism which functionally expresses BDS activity as defined herein. The invention is not limited to reliance on the ATCC No. 53968 biocatalyst and can be adapted to use with another microbial source of BDS activity, through no more than routine experimentation.

Biocatalyst (10 in FIG. 4) is prepared initially, and can comprise either a suitable suspension of intact ATCC No. 53968 microorganisms (4), a lysate thereof (6), or a substantially cell-free extract or fraction thereof (8) which contains a substantial proportion of the total BDS reactivity expressed by said microorganisms. Suitable preparation conditions for functional, BDS-expressing ATCC No. 53968 microorganisms comprise fermentation under aerobic conditions in the presence of a sulfur-free mineral salts medium (e.g., 4 g/L $K_2PO_4$, 4 g/L $Na_2HPO_4$l, 2 g/L $NH_4Cl$, 0.2 g/L $MgCl_2.6H_2O$, 0.001 g/L $CaCl_2.2H_2O$, and 0.001 g/L $FeCl_3.6H_2O$), containing a sulfur-free source of assimilable carbon such as glycerol, benzoate, acetate, glucose, ethanol, isobutanol or sucrose. In order to generate maximal biocatalytic activity, it is important that the sole source of sulfur provided to the ATCC No. 53968 bacteria comprises an organosulfur compound of the type from which assimilable sulfur can be obtained by the microorganism through BDS activity. Thus, the ATCC No. 53968 culture medium is preferably supplemented with a source of sulfur-bearing heterocycles such as thiophene, benzothiophene, the preferred model compound DBT, or derivatives thereof. A suitable organosulfur source comprises a petroleum liquid which contains organic sulfur molecules, a significant proportion of which are sulfur-bearing heterocycles.

The above medium is adjusted to a pH of from about 5 to about 8, and more preferably to between about 6 and about 7 prior to fermentation of the ATCC No. 53968 bacteria, and is maintained within this pH range during fermentation. Bacterial culture conditions further comprise fermentation generally at ambient temperature. Temperatures of from about 15° C. to about 34° C. are preferred, and temperatures between about 28° C. and 32° C. are considered particularly preferable. Growth of the culture is monitored by conventional means (e.g., turbidimetrically), until the bacteria reach the desired density per mL culture medium.

The ATCC No. 53968 bacterial culture can be separated from the culture medium and resuspended in fresh medium or other suitable buffer lacking in a source of assimilable (i.e., water-soluble, inorganic) sulfur by conventional means (comprising, e.g., settling or centrifugation). At this stage, the culture (4) can be either diluted or concentrated to a predetermined density of cells per mL.

Culture 4 can optionally be used directly as a source of biocatalyst 10. However, whereas an emulsion according to the present invention can be produced (at 16 of FIG. 4) from preparation of living or nonviable intact ATCC No. 53968 microorganisms 4 (as in Examples 1 and 2), it is preferable to prepare therefrom a BDS-active suspension of lysed microorganisms (6), substantially free of intact cells. Any lysis process, whether conventional or adapted from conventional techniques, can be used, provided that the enzyme responsible for BDS reactivity remains functional. For example, the ATCC No. 53968 bacteria can be subjected to one or more freeze-thaw cycles, treated with a suitable detergent and/or chaotropic agent, processed using a French press, or, more preferably, can be sonicated by conventional means comprising the use of a bath or immersion probe sonicator and incubation on melting ice. In this manner a microemulsion can be produced according to the present invention, wherein the minimum size of microemulsified droplets is not constrained by the dimensions of the intact individual ATCC No. 53968 organisms.

It is particularly preferred to prepare a substantially cell-free aqueous extract (8) of the microbial source of BDS reactivity, wherein the extract contains a substantial proportion of the total BDS activity functionally expressed by the microorganism. In certain suitable microorganisms, the BDS reactive enzyme may be functionally expressed as a cell envelope-associated enzyme. In the case of the ATCC No. 53968 microorganism and its functional derivatives, it was previously disclosed in U.S. Ser. 07/486,597 that BDS activity appears to arise from an enzyme associated with the exterior cell membrane and/or cell wall of the intact bacterium. The results disclosed in the Examples herein comprise the first actual demonstration of support for this postulate. Thus, a substantially cell-free extract of ATCC No. 53968, comprising cell membranes and cell membrane fragments was prepared, and found to contain a substantial proportion of the total BDS activity functionally expressed by this microorganism.

A cell free extract (8) suitable for use as biocatalyst 10 in the present BDS method can be prepared according to standard techniques, such as centrifugal fractionation, ammonium sulfate fractionation, filtration, bioaffinity or immunoaffinity precipitation, gel permeation chromatography, liquid chromatography, high pressure liquid chromatography, reverse-phase liquid chromatography, preparative electrophoresis, isoelectric focussing, and the like. For example, a centrifugal fractionation procedure is described in Example 3, wherein it is shown that a substantial proportion of ATCC No. 53968 expressed BDS reactivity is associated with the "cell debris" fraction of sonicated, lysed bacterial cells. This fraction, which comprises fragments of cell walls and/or outer cell membranes, was obtained as a pellet following centrifugation of lysed ATCC No. 53968 cells for 5 minutes at 6,000×g.

Although, as shown in FIG. 2, the selective cleavage of organic carbon-sulfur bonds in sulfur-bearing heterocycles can proceed through either oxidative or reductive pathways, it has been shown that the membrane-associated BDS activity expressed by microorganisms such as ATCC No. 53968 and derivatives thereof results in the conversion of DBT to 2-hydroxybiphenyl, and therefore involves the consumption of oxygen. See U.S. Pat. Nos. 5,104,801 and 5,132,219 and FIG. 3. It follows that the present BDS method is carried out under aerobic, rather than anaerobic, conditions.

If necessary, the aqueous source of biocatalytic activity (10 in FIG. 4) and/or the substrate petroleum liquid (12) is contacted with suitable source of oxygen 14, which comprises for example, air, oxygen-enriched air, pure oxygen, or oxygen-saturated perfluorocarbons (PFCs). The dissolved oxygen content of the aqueous biocatalyst or of the substrate petroleum liquid is increased by stirring, mixing, bubbling or sparging oxygen source 14 therethrough, until the desired concentration of dissolved oxygen is achieved. For present purposes, it is considered preferable to increase the dissolved oxygen content of at least the substrate petroleum liquid in this manner, thereby capitalizing on the greater solubility of oxygen in organic, rather than aqueous, liquids.

Aqueous source of BDS activity 10 will hereinafter be referred to as the aqueous phase and (optionally oxygenated) substrate petroleum liquid 12 will be referred to as the organic phase. The method of the present invention involves forming an emulsion, and preferably a microemulsion, between the aqueous and organic phases (16 in FIG. 4). In other words, a biphasic system is produced wherein mutually immiscible aqueous (10) and organic (12) phases are intimately interdistributed, in the form of either discrete globules (droplets), or finely layered lamellae. Either the aqueous or the organic phase, or both, can be the continuous phase of emulsion 16, depending on, inter alia, the relative volumes of each phase present in the system. Emulsions wherein the aqueous phase volume is minimized are generally preferred; thus, water-in-oil emulsions are particularly preferred. Accordingly, in the following discussion, a water-in-oil emulsion wherein aqueous droplets are dispersed within the organic phase, the latter being the continuous phase, are intended unless otherwise indicated. It will also be presumed that, in general, the density of aqueous phase 10 will exceed that of organic phase 12.

It has been noted that the method described herein can be performed using intact microorganisms (4) as the source of aqueous biocatalyst (1O). As a practical matter, in this embodiment of the invention, the minimal diameter of water droplets in a water-in-oil emulsion, and the minimal interlammelar distance in a bicontinuous emulsion, are constrained by the dimensions of the microbes themselves. Emulsions having a droplet diameter or interlamellar distance on the order of about 1 $\mu$m are therefore formed.

In preferred embodiments wherein the source of biocatalyst comprises a substantially cell-free preparation of lysed microorganisms (6), or, in particularly preferred embodiments wherein the aqueous biocatalyst is a substantially cell-free extract (8) containing a substantial proportion of the total BDS activity expressed by the source microorganism, the dimensions of oil or water droplets, or of interlamellar distance, are not subject to this constraint. Thus, microemulsions 16 of the preferred embodiments can comprise aqueous droplets significantly smaller than the dimensions of intact microorganisms. Microemulsions having a droplet diameter or interlamellar distance of less than about 1 μm are thus contemplated in the present invention. Droplet diameters or interlamellar distances in the nanometer range are preferred, due to the inverse relationship between the surface area-to-volume ratio of a given microemulsion system and the droplet diameter therein. Thus, in microemulsions having a very fine droplet size, the aqueous biocatalyst is brought into very intimate contact with the organic substrate petroleum liquid phase, with the result that the observed rate of desulfurization can be enhanced. This result is thought to be due in part to the diminished impact of partitioning of organic sulfur molecules into the aqueous phase, or conversely of the biocatalyst into the organic phase, on the observed rate of desulfurization. The optimal droplet diameter or interlamellar distance for a particular microemulsion will depend on several parameters, including the concentration and specific activity of the biocatalyst employed, as well as the concentrations of dissolved oxygen and of sulfur-bearing heterocycles present in the system. Optimal conditions for the desulfurization of a given substrate petroleum liquid according to the method described herein can be determined through no more than routine experimentation.

The emulsion or microemulsion (16) of the present invention can be produced by a variety of techniques. It is essential, of course, that biocatalyst 10 is not functionally impaired or compromised during production of microemulsion 16. For example, a suitable microemulsion can be produced by causing the aqueous and organic phases to pass simultaneously through a small aperture or series of apertures or channels (e.g., a mesh or sieve), whereby fine turbulence is produced in the combined phases, causing them to become intimately intermixed, thereby forming microemulsion 16. The turbulence should not be so great as to cause the shearing or denaturation of the biocatalyst, however. Alternatively, the phases can be introduced into a vessel and mixed, stirred or agitated until microemulsion 16 is formed. Agitation sufficient to form a microemulsion can be delivered by mechanical means, hydrodynamic means, or ultrasonic means using a conventional bath or probe sonication device.

In many embodiments, it will be desirable to accelerate the formation of emulsion or microemulsion 16 by introducing surfactant 17 to the combined phases. A surfactant is a tensioactive substance, which alters the physicochemical nature of a surface or interface, specifically by lowering facial or interfacial tension. Typically, a surfactant comprises both hydrophilic and hydrophobic moieties and is therefore soluble in both aqueous and organic liquids. Suitable surfactants for present purposes include, for example, Tween 80 ® (Sigma Chemicals), K.-I. Lee and T. F. Yen, J. (1990) Chem. Tech. Biotechnol. 48:71-79, and pentaethylene glycol dodecyl ether, K. M. Larsson et al. (1990) Biotechnol. Bioeng. 36:135-141. Biosurfactants, such as those produced by certain microorganisms, can also be used in the present invention. J. C. Bertrand (1983) Biotechnol. Lett. 5(8):567-572. In some embodiments, the microorganism comprising the source of BDS activity may also produce its own biosurfactants. See, for example, S. E. Stevens and W. D. Burgess, U.S. Pat. No. 4,851,350 (issued 1989).

It has already been pointed out that emulsions wherein the volume of the aqueous phase is minimized are preferred, and that water-in-oil emulsions and microemulsions are particularly preferred. Another particularly preferred embodiment of the present invention comprises the formation of reverse micelles at 16, which are similar to the water-in-oil system but possess a more defined, membranous surface structure. Without wishing to be limited as to the structural details pertaining to this embodiment, in the reverse micelle system, cell membrane fragments are thought to become associated with one or more types of nonionic surfactants, which comprise the "skin" of the reverse micelle structure (i.e., the interface between the aqueous and organic phases). In this manner, the enzyme responsible for observed BDS reactivity can be deployed at the optimal location within the biphasic system for access to substrate molecules, further minimizing the effects of diffusion on the observed rate of desulfurization. A suitable method of producing reverse micelles is described in K.-I. Lee and T. F. Yen, J. (1990) Chem. Tech. Biotechnol. 48:71-79.

Once emulsion or microemulsion 16 has been formed between aqueous biocatalyst 10 and organic substrate petroleum liquid 12 in need of BDS treatment, it is incubated (18) under conditions sufficient to bring about the biocatalytic cleavage of organic carbon-sulfur bonds even in sulfur-bearing heterocycles. Generally, suitable conditions comprise incubation at ambient temperatures and pressures. Incubation 18 can be carried out at any temperature greater than the pour point of the substrate petroleum liquid and less than the temperature at which the biocatalyst becomes inactivated. In certain embodiments, the incubation temperature is further defined by the thermal stability of the microemulsion. For example, microemulsions which are formed in the presence of certain surfactants will spontaneously segregate into discrete aqueous and organic phases if the temperature is either lowered below or raised above a critical value. Temperature-sensitive microemulsions are described in K. M. Larsson et al. (1990) Biotechnol. Bioeng. 36:135-141. Emulsions and microemulsions wherein the ATCC No. 53968 biocatalyst is used are preferably incubated at temperatures of from about 10° C. to about 42° C., with temperatures between about 28° C. and 32° C. being considered particularly preferable for obtaining high rates of desulfurization.

During incubation 18, emulsion or microemulsion 16 can be maintained, if desired, continuously or intermittently under turbulent conditions. An advantage of using microemulsions is that mixing may not be required: this would further enhance the economic desirability of the process disclosed and claimed herein. Turbulence can be produced, e.g., by mechanical, hydrodynamic or ultrasonic means, provided that the biocatalyst is not thereby exposed to unduly severe conditions, resulting in shearing or denaturation. For particular systems, for example where there is a high concentration of sulfur-bearing heterocycles in the organic substrate liquid, it will be desirable to continually mix or agitate the microemulsion. In this manner, one can ensure that the biocatalyst is maintained in a BDS substrate-rich (rather than reaction product-rich) local environment.

The incubation step (18) of the present BDS method is carried out for a sufficient period of time for a significant number of biocatalytic cleavages to occur. Incubation time will depend on several parameters, including the concentration and specific activity of the biocatalyst employed, the concentrations of dissolved oxygen and of sulfur-bearing heterocycles present in the system, the temperature and extent of mixing or turbulence during BDS treatment, and the scale on which BDS is carried out. It will also depend, in significant part, on the desired extent or degree of desulfurization of the petroleum liquid.

Preferably, incubation times for embodiments of the present invention wherein the ATCC No. 53968 biocatalyst is relied upon will not be substantially longer than about one or two days. When this biocatalyst is used, significant desulfurization can be observed following incubation periods of as little as about 16 hours (see Example 2). Incubations should not be so lengthy that undesirable side reactions occur, however, and incubations lasting beyond the point at which significant BDS activity ceases (e.g., once the concentration of sulfur-bearing heterocycles has become too small for the desulfurization reaction to proceed in the forward direction, liberating sulfur) are not preferred. Appropriate incubation times for the desired degree of desulfurization of a given substrate petroleum liquid according to the method presently described can be determined through no more than routine experimentation.

Suitable incubation conditions and periods can be determined by monitoring the progress of biocatalytic desulfurization of the petroleum liquid, using conventional techniques which are readily available to those skilled in the art. For example, baseline samples can be collected from the organic substrate petroleum liquid before it is combined with the present biocatalytic agent. Thereafter, samples can be withdrawn from the incubation mixture (the emulsion or microemulsion) at desired intervals of time. Time course profiles can be constructed and can be used to calculate the optimal incubation conditions and times for the BDS treatment particular types and volumes of petroleum liquids. It will generally be preferred to collect post-BDS samples from the desulfurized petroleum liquids, to confirm desulfurization to the desired extent.

The disappearance of sulfur from particular substrate organosulfur compounds such as DBT and related heterocycles can be monitored using a gas chromatograph coupled with an appropriately calibrated X-ray fluorescence detector(GC/XRF), flame photometric detector (GC/FPD), ion trap detector (GC/ITD), mass spectrometer (GC/MS), nuclear magnetic resonance spectrometer (GC/NMR), infrared spectrometer (GC/IR), or atomic emission spectrometer (GC/AES, also known as a flame spectrometer), in conjunction with one or more appropriate molecular standards. Methods which allow the operator to directly visualize the disappearance of sulfur atoms from combustible hydrocarbons are preferred. Thus, X-ray fluorescence and flame spectrometry detection systems are particularly preferred.

The above detection systems can also be used in the absence of prior gas chromatographic isolation of the selected organosulfur compound, to measure the decrease in total organic sulfur in the substrate fossil fuel. Again detection systems such as X-ray fluorescence and flame spectrometry are preferred for these purposes, as they allow the direct visualization of sulfur atoms. If this type of rapid analysis is to be used, it will be important to ensure that the sulfur being measured is in fact organic sulfur. Thus, any accumulated water-soluble sulfur products of the biocatalytic reaction (e.g., sulfate) must be separated from the sample prior to analysis.

Once the desired degree of biocatalytic desulfurization has been attained, it will generally become desirable to recover the desulfurized petroleum liquid (22 in FIG. 4) from the emulsion, microemulsion or reverse micelles of the present invention. Accordingly, in preferred embodiments, a reversible or transient microemulsion is employed. Thus, microemulsions which become segregated (at 20) into substantially discrete aqueous and organic phases upon exposure to particular conditions or agents are considered desirable, and irreversible microemulsions such as those known in the art as "mousses" are not preferred.

The precise conditions or agents which are sufficient to cause phase segregation 20 will depend upon the components and characteristics of the particular emulsion formed. For example, some emulsion systems will spontaneously segregate into aqueous and organic phases unless continually subjected to agitation or turbulence. Such emulsions are reversed by maintaining them under stationary conditions for a sufficient period of time for segregation to occur. Other emulsions and microemulsions are sensitive to the relative volumes of aqueous and organic phases present. These microemulsions can be reversed by, e.g., adding an excess amount of an aqueous liquid. In these circumstances, it is preferable to add a liquid free of water-soluble sulfur, such that the water-soluble sulfur (e.g., sulfate) produced during biocatalysis will be extracted into the aqueous phase.

Still other types of microemulsions can be reversed by treatment with a chemical agent. For example, a demulsifying agent which increases the interfacial tension between the aqueous and organic phases can be used to bring about coalescence of individual aqueous droplets or reverse micelles, leading to the pooling and sedimentation of aqueous phase droplets. If a surfactant (17) has been used to produce the microemulsion, the demulsifying agent can be one which deprives the surfactant of its properties, e.g., by rendering it insoluble in either the aqueous or the organic phase.

Yet another class of emulsions and microemulsions can be caused to reverse upon exposure to particular physical conditions. For example, K. M. Larsson et al. (1990) Biotechnol. Bioeng. 36:135–141 describe temperature-sensitive microemulsion systems, wherein phase segregation occurs upon heating or cooling to a particular temperature. In the case of a microemulsion formed in the presence of the nonionic surfactant pentaethylene glycol dodecyl ether, phase segregation has been reported to occur upon cooling, from 27.5° C. to 18° C., of a water-in-oil microemulsion comprising a four-fold excess of organic phase volume to aqueous phase volume (Larsson et al., p. 139).

In certain embodiments, the rate of phase segregation 20 of a transient or reversible microemulsion can be accelerated by, for example, centrifuging the microemulsion to enhance the coalescence and sedimentation of aqueous phase droplets. Alternatively, a particulate solid having a wettable surface can be introduced to the microemulsion, thereby providing nucleation sites for the condensation of the aqueous phase. Sedimentation of the particulate solid thus coincides with the sedimentation of the aqueous phase.

Reverse micelles produced according to the present invention can be disrupted when exposed to particular conditions, essentially as described above in connection with the reversal of water-in-oil microemulsions. Appropriate disruption conditions can be determined through no more than routine experimentation.

Regardless of which of the above-described embodiments of the present invention has been employed, the products of phase segregation 20 will be a desulfurized petroleum liquid (22) and an aqueous phase (24), usually comprising biocatalyst and inorganic sulfur which has been liberated from the substrate petroleum liquid as a result of biocatalytic desulfurization.

The invention will now be further illustrated by the following representative Examples.

EXAMPLE 1

Biocatalytic Desulfurization in a Model System with the Emulsifying Agent Triton N-101.

A model substrate petroleum liquid was prepared by diluting DBT into hexadecane to a final concentration of 3% DBT or 0.52% organic sulfur. Five culture flasks, designated A-E, received 10 mL samples of the substrate petroleum liquid. To Flask A, 30 mL sulfur-free mineral salts medium was added. Flasks B-E received instead 30 mL portions of a suspension of *R. rhodochrous* ATCC No. 53968 in sulfur-free mineral salts medium. Thereafter, the culture flasks were adjusted to the final concentrations of the commercial emulsifier Triton ® N-101 (Dow Chemical Co.) shown below in Table 1. The flasks were maintained at 30° C. and shaken at 250 rpm for 40 hours, after which samples of the oil phase were withdrawn and analyzed for sulfur content according to standard methods. The results of this study are shown below in Table 1.

TABLE 1

Biocatalytic Desulfurization in a Model System containing the Emulsifier Triton ® N-101

| Biocatalyst | Emulsifier | % Sulfur | % Desulfurization |
|---|---|---|---|
| − | − | 0.513 | — |
| + | − | 0.485 | 5.07 ± 0.005 |
| + | 0.05% | 0.486 | 5.07 ± 0.005 |
| + | 0.10% | 0.487 | 5.07 ± 0.005 |
| + | 0.50% | 0.473 | 7.89 ± 0.009 |

These results show that biocatalytic desulfurization can be carried out in the presence of the commercial emulsifying agent Triton ® N-101. This study further demonstrates that the extent of biocatalytic desulfurization can be significantly increased upon the formation of an appropriate emulsion.

EXAMPLE 2

Enhanced Performance of Biocatalytic Desulfurization of a Residual Fuel Oil in an Emulsion.

A residual fuel oil was introduced to six culture flasks, designated A-E. Sulfur-free mineral salts medium was added to flasks A and D. A suspension of *R. rhodochrous* ATCC No. 53968 in sulfur-free mineral salts medium was added to flasks B, C, E and F. Flasks A, C, D and F further received an emulsifying agent, sufficient to form an appropriate emulsion between the residual fuel oil and the aqueous phase. Thereafter, the flasks were agitated vigorously, A, B, and C for 16 hours, and D, E and F for 24 hours. Following this incubation period, the percent-sulfur of the treated oil was analyzed according to standard methods. The results of this study are shown below in Table 2, wherein percent desulfurization of each sample has been calculated relative to the percent-sulfur content of the starting material (the untreated residual fuel oil, at 4.76% S).

TABLE 2

Effect of Added Emulsifier on the Biocatalytic Desulfurization of a Residual Fuel Oil

| Biocatalyst | Treatment Time | Emulsifier | % Sulfur | % Desulfurization |
|---|---|---|---|---|
| − | 16 hours | + | 5.06 | — |
| + | 16 hours | − | 4.88 | none |
| + | 16 hours | + | 3.30 | 31% |
| − | 24 hours | + | 5.58 | — |
| + | 24 hours | − | 4.84 | none |
| + | 24 hours | + | 3.60 | 25% |

These results show that biocatalytic desulfurization can be enhanced when an appropriate emulsion between the organic (substrate) and aqueous (biocatalyst) phases is formed. The results of this study can be interpreted as consistent with the postulate that intimateness of contact between the oil and water phases is rate-limiting in the biocatalytic desulfurization of a substrate petroleum liquid.

EXAMPLE 3

Biocatalytic Desulfurization Using a Cell-Free Extract

A culture of *R. rhodochrous* ATCC No. 53968, was prepared by standard fermentation methods. The intact bacterial cells were disrupted or lysed by sonication using an MSE brand sonicator equipped with a 16 mm diameter probe. The progress of cell lysis was monitored by tracking the appearance of soluble proteins (using a standard Bradford protein assay kit, such as that marketed by BioRad, according to the manufacturer's directions). Maximal protein release (indicating maximal lysis) from a concentrated suspension of intact ATCC No. 53968 bacteria was observed following 4-6 cycles of sonication (wherein one cycle comprises 30 seconds of sonication followed by a 30 second incubation on melting ice).

The preparation of lysed bacteria was then fractionated by centrifugation. A "cell debris" fraction (comprising cell wall fragments) was obtained as a pellet following centrifugation for 5 minutes at 6,000×g. This fraction was demonstrated to contain biocatalytic desulfurization activity, as determined by Gibb's assay for the presence of 2-hydroxybiphenyl (2-HBP), the observed hydrocarbon product of oxidative biocatalytic desulfurization of DBT by ATCC No. 53968. The procedure for Gibb's assay was as follows:

Cell or cell fraction harvest. Cells or cell envelope fraction was centrifuged in a Sorvall GSA or ss34 rotor at 8,000×g for 20 minutes at room temperature. The resulting pellet was washed in 0.05 M phosphate buffer, pH 8.0, and resuspended in the same buffer. A sample was withdrawn and diluted 1:10 or 1:20 in phosphate buffer, and the optical absorbance of the suspension at 600 nm was determined. Thereafter, the volume was adjusted to yield a suspension having an $A_{600}$ in excess of 3.0, and preferably of about 4.0. This concentration was verified by withdrawing a sample, diluting it 1:10 and confirming its $A_{600}$ in the range of 0.300-0.400.

BDS incubation. Enzyme reactions were conducted in small flasks or large-diameter test tubes, which provide adequate volume for agitation/aeration. All reactions were in excess of about 5 mL. For each reaction, approximately 1 mg DBT was added per mL of cell-/cell envelope suspension (a 5 mM addition of DBT to a 25 mL reaction requires 23 mg DBT; thus, reactions were adjusted to contain about 5 mM enzyme substrate). Reaction mixtures were transferred to a 30° C. water bath, and subjected to agitation at 200 rpm. It was noted that there is an initial lag in BDS activity; therefore, a zero time sample was considered optional. After 1, 2 and 3 hours of incubation, 1.5 mL samples were withdrawn from each reaction mixture and pelletted at about 12,000 rpm for 4 minutes in an Eppendorf microfuge. One milliliter samples of the resulting supernatants were transferred to 1.5 mL Eppendorf tubes for assay. It was found that these supernatant samples could be stored at 4° C. for several days prior to assay, if desired.

Gibb's assay. 0.1 g Gibb's reagent (2,6-dichloro-quinone-4-chloroimide; obtained from Sigma Chemical Co.) was dissolved in 10 mL absolute ethanol in a test tube, and promptly protected from light by wrapping the tube in foil. This solution was prepared freshly each day. To each Eppendorf tube containing 1.0 mL supernatant adjusted to pH 8.0, 10 $\mu$L Gibb's reagent was added. After a 30 minute incubation at room temperature, the appearance of the blue product of reaction between Gibb's reagent and 2-HBP was monitored by measuring the increase in optical absorbance of the assay mixture at 610 nm, relative to the $A_{610}$ of a sample containing phosphate buffer rather than supernatant. Results were expressed as units of absorbance per hour, per unit of cell material (one unit of cell material is defined as the amount of cell/cell envelope suspension which, when suspended in water, yields an $A_{600}$ of 1.0).

Results of this study are summarized in Table 3.

TABLE 3

Biocatalytic Desulfurization by intact cells, lysed cells, and a cell-free fraction

| Biocatalyst | Change in Absorbance (610 nm) per Hour per Unit Cell Material | Number of Determinations |
|---|---|---|
| Washed intact cells | 0.085 ± 0.007 | n = 4 |
| Freeze-Thaw lysed cells (unfractionated) | 0.060 ± 0.001 | n = 2 |
| Sonicated lysed cells (cell debris fraction) | 0.035 ± 0.002 | n = 2 |

These results demonstrate that a substantial proportion of the total biocatalytic desulfurizing activity expressed by the ATCC No. 53968 microorganism is found in the "cell debris fraction", which contains external cell membrane and cell wall fragments. Without wishing to be limited as to the location, structure or identity of the functional enzyme responsible for the observed results, the data presented above can be interpreted as indicating that, at least for this particular microorganism, the enzyme biocatalyst responsible for desulfurization is a component of the cell envelope (comprising the bacterial cell wall and cell membrane).

EQUIVALENTS

Those skilled in the art will recognize, or be able to ascertain using no more than routine experimentation, many equivalents to the specific embodiments of the invention described herein. These and all other such equivalents are intended to be encompassed by the following claims.

We claim:

1. A method for desulfurizing a petroleum liquid which contains organic sulfur molecules, through the use of an aqueous catalytic agent, wherein the catalytic agent comprises a cell-free enzyme preparation from *Rhodococcus* sp. ATCC 53969, *Bacillus sphaericus* ATCC 53969, or a mutant thereof having the ability to selectively cleave organic carbon-sulfur bonds including those in sulfur-bearing heterocycles, comprising the steps of:
   a) forming a microemulsion between the petroleum liquid and the aqueous catalytic agent; and
   b) incubating the microemulsion under conditions sufficient to bring about the catalytic cleavage of organic carbon-sulfur bonds for a sufficient period of time for a significant number of catalytic cleavages to occur, whereby the organic sulfur content of the petroleum liquid is significantly reduced, thereby producing a desulfurized petroleum liquid.

2. The method of claim 1 wherein the catalytic agent comprises cell envelope and cell envelope fragments having associated therewith the enzyme.

3. The method of claim 2 wherein the enzyme directs the oxidative cleavage of said bonds.

4. The method of claim 3 wherein the enzyme directs the sulfur-selective oxidative cleavage of said bonds.

5. The method of claim 3 wherein the microorganism which functionally expresses the enzyme is *Rhodococcus* sp. ATCC 53968.

6. The method of claim 1 wherein the continuous phase of the microemulsion is the aqueous phase.

7. The method of claim 1 wherein the continuous phase of the microemulsion is the organic phase.

8. The method of claim 1 wherein the microemulsion is reversible, the method including the additional steps of:
   c) exposing the microemulsion to conditions sufficient to reverse said microemulsion, whereby an aqueous phase comprising the biocatalyst and an organic phase comprising the desulfurized petroleum liquid are obtained; and
   d) separating the desulfurized petroleum liquid from the aqueous phase.

9. A method for desulfurizing a petroleum liquid which contains organic sulfur molecules through the use of an aqueous biocatalytic agent comprising a substantially cell-free extract of *Rhodococcus* sp. 53968, *Bacillus sphaericus* ATCC 53969 or a mutant thereof which functionally expresses an enzyme capable of selectively cleaving organic carbon-sulfur bonds including those in sulfur-bearing heterocycles, wherein the extract contains a substantial proportion of the total activity of said enzyme expressed by the microorganism, the method comprising the steps of:
   a) forming a microemulsion between the petroleum liquid and the aqueous biocatalytic agent; and
   b) incubating the microemulsion under conditions sufficient to bring about the biocatalytic cleavage of organic carbon-sulfur bonds including those in sulfur-bearing heterocycles, for a sufficient period of time for a significant number of biocatalytic cleavages to occur, whereby the organic sulfur content of the petroleum liquid is significantly reduced, thereby producing a desulfurized petroleum liquid.

10. The method of claim 9 wherein the substantially cell-free extract comprises cell envelope and cell envelope fragments having associated therewith the enzyme.

11. The method of claim 10 wherein the enzyme directs the oxidative cleavage of said bonds.

12. The method of claim 11 wherein the enzyme directs the sulfur-selective oxidative cleavage of said bonds.

13. The method of claim 11 wherein the microorganism which functionally expresses the enzyme is Rhodococcus sp. ATCC 53968.

14. The method of claim 9 wherein the continuous phase of the microemulsion is the aqueous phase.

15. The method of claim 9 wherein the continuous phase of the microemulsion is the organic phase.

16. The method of claim 9 wherein the microemulsion is reversible, the method including the additional steps of:
   c) exposing the microemulsion to conditions sufficient to reverse said microemulsion, whereby an aqueous phase comprising the biocatalyst and an organic phase comprising the desulfurized petroleum liquid are obtained; and
   d) separating the desulfurized petroleum liquid from the aqueous phase.

17. A method for desulfurizing a petroleum liquid which contains organic sulfur molecules through the use of providing an aqueous biocatalytic agent comprising a substantially cell-free envelope or envelope fragment-containing extract of Rhodococcus sp. ATCC 53968, *Bacillus sphaericus* ATCC 53969, or a mutant thereof which functionally expresses a membrane-associated enzyme capable of selectively cleaving organic carbon-sulfur bonds including those in sulfur-bearing heterocycles, wherein the extract contains a substantial proportion of the total activity of said enzyme expressed by the microorganism, the method comprising the steps of:
   a) forming reverse micelles of the aqueous biocatalytic agent in the petroleum liquid; and
   b) incubating the reverse micelles under conditions sufficient to bring about biocatalytic cleavage of organic carbon-sulfur bonds including those in sulfur-bearing heterocycles, for a sufficient period of time for a significant number of biocatalytic cleavages to occur, whereby the organic sulfur content of the petroleum liquid is significantly reduced, thereby producing a desulfurized petroleum liquid.

18. The method of claim 17 wherein the enzyme directs the sulfur-selective oxidative cleavage of aid bonds.

19. The method of claim 17 wherein the microorganism which functionally expresses the enzyme is Rhodococcus sp. ATCC 53968.

20. The method of claim 17, further including the additional steps of:
   c) exposing the reverse micelles to conditions sufficient to disrupt them, whereby an aqueous phase comprising the biocatalyst and an organic phase comprising the desulfurized petroleum liquid are obtained; and
   d) separating the desulfurized petroleum liquid from the aqueous phase.

* * * * *